(12) United States Patent
O'Neil et al.

(10) Patent No.: US 7,514,539 B2
(45) Date of Patent: Apr. 7, 2009

(54) EPITOPE DIRECTED SELECTION OF ANTIBODIES TO MURINE TISSUE FACTOR

(75) Inventors: Karyn O'Neil, Kennett Square, PA (US); Raymond Sweet, Bryn Mawr, PA (US)

(73) Assignee: Centocor, Inc., Malvern, PA (US)

( * ) Notice: Subject to any disclaimer, the term of this patent is extended or adjusted under 35 U.S.C. 154(b) by 325 days.

(21) Appl. No.: 11/112,481

(22) Filed: Apr. 22, 2005

(65) Prior Publication Data

US 2006/0039900 A1 Feb. 23, 2006

Related U.S. Application Data

(60) Provisional application No. 60/565,674, filed on Apr. 26, 2004, provisional application No. 60/565,633, filed on Apr. 26, 2004.

(51) Int. Cl.
*C07K 16/00* (2006.01)
(52) U.S. Cl. .............................. 530/388.25; 530/388.1; 530/387.3; 424/133.1; 424/141.1; 424/145.1
(58) Field of Classification Search ........................ None
See application file for complete search history.

(56) References Cited

U.S. PATENT DOCUMENTS

| | | | |
|---|---|---|---|
| 5,223,427 A | 6/1993 | Edgington et al. | |
| 5,853,724 A | 12/1998 | Garrity et al. | |
| 5,986,065 A * | 11/1999 | Wong et al. | 530/388.22 |
| 6,001,978 A | 12/1999 | Edgington et al. | |
| 6,376,170 B1 | 4/2002 | Burton et al. | |
| 6,589,758 B1 | 7/2003 | Zhu | |
| 2003/0176664 A1 * | 9/2003 | Jiao et al. | 530/389.2 |

FOREIGN PATENT DOCUMENTS

| | | |
|---|---|---|
| WO | WO96040921 | 12/1996 |
| WO | WO9953049 A1 | 10/1999 |
| WO | WO0202773 A2 | 1/2002 |

OTHER PUBLICATIONS

Price et al. Anaesthesia 2004, 59:483-492.*
Fay et al., Blood Reviews 2005, 19:15-27.*
Janeway et al., Immunobiology, third edition, 1997, Garland Press, pp. 3:7-3:11.*
Rudikoff et al. PNAS USA, 1982, 79:1979-1983.*
Horn, IR et al. "Selection of phage-displayed Fab antibodies on the active conformation of Ras yields a high affinity conformation . . . " FEBS Lett. 463:115-120, Dec. 10, 1999.
Hoogenboom, HR & Chames, P. Natural and desinger binding sites made by phage display technology Immunol Today 21(8): 371-378, 2000.
Huang, M et al. The mechanism of an inhibitory antibody on TF-initiated blood coagulation revealed by crystal structures . . . J Mol Biol 275:873-894, 1998.
Kretzschmar, T & von Rueden, T. "antibody disocery: phage display" Curr Opin Biotechnol 13:598-602, Oct. 31, 2002.
Ke, S-H. Distinguishing the Specificities of Closely Related Proteases J Biol Chem 272(26): 16603-9, Jun. 27, 1997.
Kirkham, PM et al. "Towards the design of an antibody that recognizes a specific epitope" J Mol Biol 285:909-5, 1999.
Osbourn, JK. "Pathfinder selection: in situ isolation of novel antibodies" Immunotechnol 3:293-302, 1998.
Parsons, HL et al. "Directing phage selections trowards specific epitopes" Protein Engineering 9(11): 1043-1049, 1996.
Tsui, P. et al. Progressive epitope-blocked panning of a phage library for isolation of human RSV antibodies. J Immunological Methods 263(2002): 123-132, 2002.
Van Ewijk, W et al. "Subtractive isolation of phage-displayed single-chain antibodies . . . " Proc Natl Acad Sci USA 94:3903-3908, Apr. 1997.
Key, NA; Bach, RR. "Tissue factor as a therapeutic target." Thromb Heamost. 85:375-6, 2001.
Kirchhofer, D. et al. "Epitope location on tissue factor determines the anticoagulant potency of monoclonal anti-tissue factor antibodies." Thromb Haemost 84:1072-81, 2000.
Morrissey et al., "Tissue factor: an enzyme cofactor and true receptor." Thromb. Heamost 86:66-74, 2001.
Ruf W. Edgington TS. An anti-tissue factor monoclonal antibody which inhibits TF.VIIa complex is a potent anticoagulant in plasma. Thromb Haemost 66(5):529-33, Nov. 1, 1991.

* cited by examiner

*Primary Examiner*—Michael Szperka
(74) *Attorney, Agent, or Firm*—Kenneth J. Dow

(57) ABSTRACT

A tissue factor antibody which binds to non-human tissue factor and is useful as a surrogate in preclinical testing where the human therapeutic tissue factor candidate antibody does not interact with the homolog target protein in a manner that would provide meaningful information about treatment efficacy or safety.

3 Claims, 9 Drawing Sheets

Fig. 1
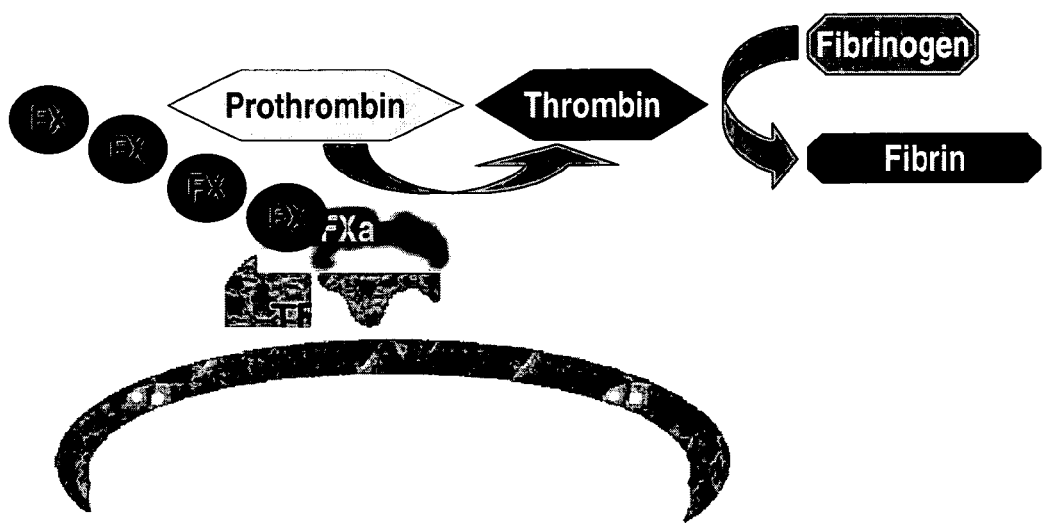
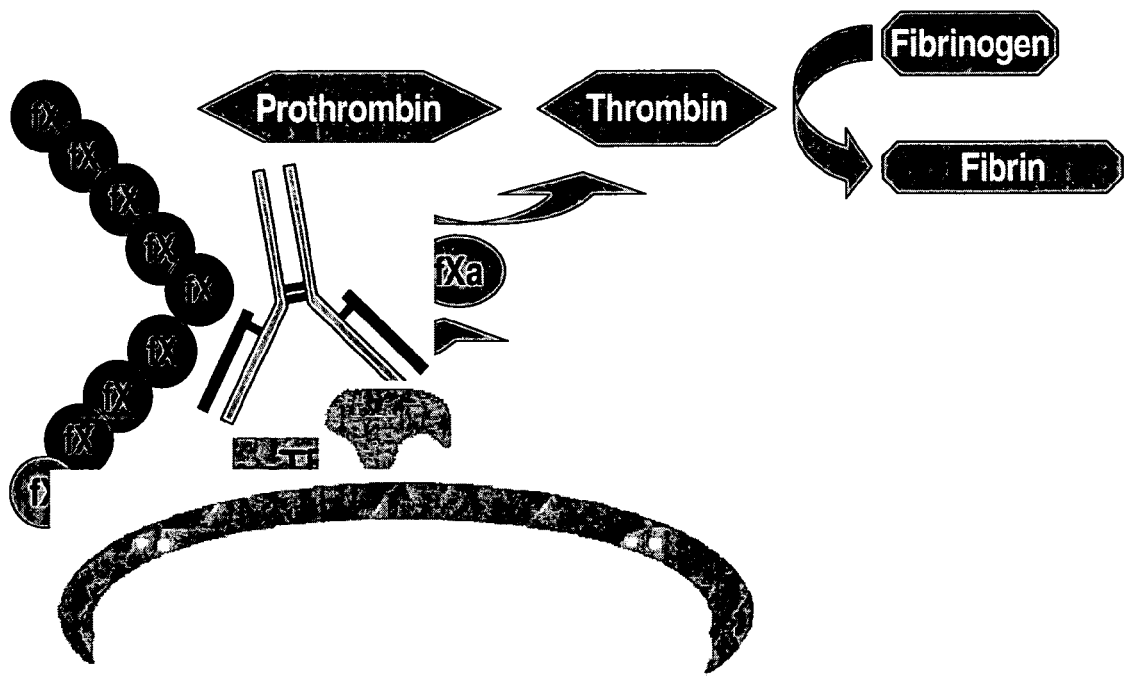

Fig. 3

| | | |
|---|---|---|
| h Tissue Factor EC Domain | (1) | SGTTNTVAAYNLTWKSTNFKTILEWEPKPVNQVYTVQISTKSGDWKSKCF |
| m TF EC Domain | (1) | ---GIPEKAFNLTWISTNFKTILEWQPKPVNQVYTVQISTKSGDWKSKCF |
| Consensus | (1) | AFNLTW ST EKTILEW PKP N YTVQIS KS WK KCF |
| h Tissue Factor EC Domain | (51) | YTTDTECDLTDEIVKDVKQTYLARVFSYPAG------VESTGSAGEPLYENSPEF |
| m TF EC Domain | (48) | SLTDTECDLTDEIVKDVTWANELLPVRREISVHGDGQLVIHEAEPPA EP E |
| Consensus | (51) | TTDTECDLTDEIVKDV Y AKV S P N A EP E |
| h Tissue Factor EC Domain | (95) | ENREETEPLNAPTRSETWQVTTENFYTTECDLTDEIVK |
| m TF EC Domain | (98) | TQKLKLERVLQRGRANVKDSLTTECDLTDEIVK |
| Consensus | (101) | NAP F PY DTNLGQP IQ FEQ G KLNV V D TLVRKN TFLSLR |
| h Tissue Factor EC Domain | (145) | DREKTYYWISSEQAKELTKENIDYSEVSFCQAP |
| m TF EC Domain | (148) | QIEGITTRGENIPVNSEVSFCQAF |
| Consensus | (151) | VFGKDL Y I Y K SSSGKKT TNTNEF IDVD G YCF VQAMI |
| h Tissue Factor EC Domain | (195) | TVNRKSTDSPVELGEGEFRE |
| m TF EC Domain | (198) | EKTNQNPGSTVSTEWSFLG- |
| Consensus | (201) | SR N S S C Q K |

Fig. 4

| PHD | SEQ ID NO: | Framework | Heavy Chain CDR1 | CDR2 | CDR3 | SEQ ID NO | Framework | Light Chain CDR1 | CDR2 | CDR3 |
|---|---|---|---|---|---|---|---|---|---|---|
| 103 | 5 | VH5 | GYSFSNSWIA | GIIGPGHSYTKYSPSFQG | INMGYFDY | 6 | V$_{kappa}$3 | SGDSLGLKKEVS | DDSNRPS | GTYDQTIGHDV |
| 104 | 7 | VH5 | YSFTSNWIG | WIYPSDSMTRYSPSFQG | YLFGLFDN | 8 | V$_{kappa}$3 | SGDNLGSYYVS | NDNNRPS | ATYDSSTD |
| 126 | 9 | VH5 | YSFSNYWIG | FIDPDDSDTNYSPSFQG | ALYMQGGSFDS | 10 | V$_{kappa}$3 | SGDNLGSYYVS | RDTDRPS | QSYDYGVSNQ |
| 127 | 11 | VH5 | YSFTNSWIS | IIDPDDSYTSYSPSFQG | GAGYGRMFGDV | 12 | V$_{kappa}$3 | SGDNLGSYYAS | QDDNRPS | GAYTYSTSW |
| 130 | 13 | VH2 | GLSLSTSGVGVG | LIYSNDDKRYSTSLKT | YKQETIDY | 14 | V$_{kappa}$3 | SGDNLGEKYAY | DDNNR | QSYDIEIT |

Framework Sequences:

VH5: QVQLVQSGAEVKKPGESLKISCKGS CDR1 WVRQMPGKGLEWMG CDR2
QVTISADKSISTAYLQWSSLKASDTAMYYCAR CDR3 WGQGTLVTVSS

VH2: QVQLKESGPALVKPTQTLTLTCTFS CDR1 WIRQPPGKALEWLA CDR2
RLTISKDTSKNQVVLTMTNMDPVDTATYYCAR CDR3 WGQGTLVTVSS

V$_{kappa}$3: DIELTQPPSVSVAPGQTARISC CDR1 WYQQKPGQAPVLVIY CDR2
GIPERFSGSNSGNTATLTISGTQAEDEADYYC CDR3 VFGGGTKLTVLG

EPITOPE DIRECTED SELECTION OF ANTIBODIES TO MURINE TISSUE FACTOR

The present application claims the benefit of priority to U.S. Provisional Application Ser. No. 60/565,674 and U.S. Provisional Application Ser. No. 60/565,633 filed Apr. 26, 2004 the contents of which are completely incorporated by reference. The application submitted herewith contains a Sequence Listing on computer readable disk which material is hereby incorporated by reference.

BACKGROUND OF THE INVENTION

1. Field of the Invention

The present invention relates to antibodies to murine Tissue factor (mTF) that bind to one or more epitopes in the amino acid sequences of mTF that are in the same region as the epitope or epitopes to which the antibody 5G9 binds in human Tissue Factor and thus have properties similar to the 5G9 antibody. The murine antibodies of the invention are useful as research tools for evaluating the therapeutic potential of anti-tissue factor antibodies that neutralize TF activity by inhibiting the activation of Factor X and for exploring the role of TF in various biological processes.

2. Background

The coagulation of blood involves a cascading series of reactions leading to the formation of fibrin. The coagulation cascade consists of two overlapping pathways, both of which are required for hemostasis. The intrinsic pathway comprises protein factors present in circulating blood, while the extrinsic pathway requires tissue factor (TF), which is expressed on the cell surface of a variety of tissues in response to vascular injury (Davie et al., 1991, Biochemistry 30:10363). When exposed to blood, TF sets in motion a rapid cascade of activation steps that result in the formation of an insoluble fibrin clot (See FIG. 1).

TF has been investigated as a target for anticoagulant therapy. TF (also known as thromboplastin, CD142 and coagulation factor III) is a single chain, 263 amino acid membrane glycoprotein that functions as a receptor for factor VII and VIIa and thereby initiates the extrinsic pathway of the coagulation cascade in response to vascular injury. TF is an integral membrane protein normally present on the cell surface of non-vascular cell types. Healthy endothelial cells lining normal blood vessels do not produce TF, however, TF is always present in the adventitia of blood vessels.

TF serves as both a cofactor for factor VIIa, forming a proteolytically active TF:VIIa complex on cell surfaces, and as a Vila receptor, inducing downstream intracellular changes (Bazan, J F, Proc. Natl. Acad. Sci USA (1990) 87:6934-8; Reviewed by Konigsberg, et al. Thromb. Haemost. (2001) 86:757-71). In addition to its role in the maintenance of hemostasis by initiation of blood clotting, TF has been implicated in pathogenic conditions. Specifically, the synthesis and cell surface expression of TF has been implicated in vascular disease (Wilcox et al, 1989, Proc. Natl. Acad. Sci. 86:2839) and gram-negative septic shock (Warr et al., 1990, Blood 75:1481). Furthermore, in a number of pathological states involving an acute inflammatory response and progression to a thrombotic state, such as sepsis, increased TF expression on the vascular endothelium results from the release of inflammatory mediators such as s TNF and/or IL-1.

The Role of TF in Cancer

Tissue factor is also overexpressed on a variety of malignant tumors and isolated human tumor cell lines, suggesting a role in tumor growth and survival. TF is not produced by healthy endothelial cells lining normal blood vessels but is expressed on these cells in tumor vessels. It appears to play a role in both vasculogenesis in the developing animal and angiogenesis in normal and malignant adult tissues. Inhibition or targeting of TF may therefore be a useful anti-tumor strategy that could affect the survival of TF overexpressing tumor cells directly by inhibiting TF mediated cellular signaling or other activities. In addition, this approach may prevent tumor growth indirectly via an antiangiogenic mechanism by inhibiting the growth or function of TF expressing intra-tumoral endothelial cells.

WO94/05328 discloses the use of anti-TF antibodies to inhibit the onset and progression of metastasis by abolishing the prolonged adherence of metastazing cells in the microvasculature thereby inhibiting metastasis, but does not disclose any effect on the growth of established tumor cells.

The Role of TF in Transplantation

Despite the central role of TF in blood coagulation, the mechanisms underlying the regulation of TF pro-coagulant activity in vivo are still being explored as are non-coagulant activities related to receptor signaling (Morrissey, J. H. Thromb Haemost 2001; 86:66-74 and Key, N. S., Bach, R. R. Thromb Haemost 2001; 85:375-6).

Unperturbed cells in culture have weak coagulant activity, however, cells or tissues that have been disrupted or stimulated with e.g. growth factors or endotoxin leading to increased intracellular calcium ion (Ca++) display fully expressed and active TF. Perturbation of the phospholipid species between the inner and outer cell membrane leaflets, especially phosphatidyl serine, was implicated as a possible trigger of this de-encryption of a macromolecular substrate binding site on TF which defines TF activation (Bach, R. R, Moldow, C. F. Blood 1997; 89 (9): 3270-3276).

A number of reports implicate the role of active TF in the pathogenesis of transplant failure. U.S. Pat. No. 6,387,366 notes that bone marrow stem cell (BMSC) transplantation causes blood clotting or hemorrhage due to the expression of TF on the infused cells and suggests several methods to reduce the biological activity of TF or FVII in infusions employing BMSC transplantation, gene therapies employing BMSC, and other types of cell transplantation. These methods include treating the preparation or the patient with TF antagonists.

TF Antagonists

Various anti-TF antibodies are known. For example, Carson et al, Blood 70:490-493 (1987) discloses a monoclonal antibody prepared from hybridomas produced by immunizing mice with human TF purified by affinity chromatography on immobilized factor VII. Ruf et al, (1991, Thrombosis and Haemostasis 66:529) characterized the anticoagulant potential of murine monoclonal antibodies against human TF. The inhibition of TF function by most of the monoclonal antibodies that were assessed was dependent upon blocking the formation or causing the dissociation of the TF/VIIa complex that is rapidly formed when TF contacts plasma. Such antibodies were thus relatively slow inhibitors of TF in plasma as factor VII/VIIa remains active. One monoclonal antibody, TF8-5G9, was capable of inhibiting the TF/VIIa complex by blocking the F.X binding site without dissociating the complex, thus providing an immediate anticoagulant effect in plasma which is not absolute as F.VII is still available (See FIG. 1). This antibody is disclosed in U.S. Pat. Nos. 6,001,978, 5,223,427, and 5,110,730. Ruf et al. suggest that mechanisms that inactivate the TF/VIIa complex, rather than prevent its formation, may provide strategies for interruption of coagulation in vivo. In contrast to other antibodies that inhibit factor VII binding to TF, TF8-5G9 shows only subtle and indirect effects on factor VII or factor VIIa binding to the receptor. TF8-5G9 binds to defined residues of the extracellular domain of TF that are also involved in F.X binding with a nanomolar-binding constant (See FIG. 2) Thus, TF8-5G9 is able to effectively block the subsequent critical step in the coagulation cascade, the formation of the TF:VIIa:X ternary initiation complex (Huang et al, J. Mol. Biol. 275:873-894 1998).

Anti-TF monoclonal antibodies have been shown to inhibit TF activity in various species (Morrissey et al, Throm. Res. 52:247-260 1988) and neutralizing anti-TF antibodies have been shown to prevent death in a baboon model of sepsis (Taylor et al, Circ. Shock, 33:127 (1991)), and attenuate endotoxin induced DIC in rabbits (Warr et al, Blood 75:1481 (1990))

WO 96/40921 discloses CDR-grafted anti-TF antibodies derived from the TF8-5G9 antibody. Other humanized or human anti-TF antibodies are disclosed in Presta et al, Thromb Haemost 85:379-389 (2001), EP1069185, U.S. Pat. No. 6,555,319, WO 01/70984 and WO03/029295.

An antibody that specifically recognizes TF and inhibits coagulation may provide a useful therapy for diseases where thrombogenesis is abnormal. However, to evaluate the potential efficacy of an anti-TF antibody in vivo, the antibody must cross react with TF from the animal or a surrogate must be identified that acts in a similar manner to the anti-human TF antibody. In vitro experiments have demonstrated that the anti-human TF antibody, 5G9, does not bind to murine TF. This observation is consistent with the structural data and with the differences in the mouse and human proteins in the region that constitutes the 5G9 epitope. Indeed, there are eight residues within the epitope that are different between murine and human TF (FIG. 3). Efforts to generate an anti-murine TF antibody that acts in a manner similar to 5G9 by immunization of rats or other animals have not heretofore been successful.

Phage display technology describes an in vitro selection technique in which the polynucleotide sequence encoding a peptide or protein is genetically fused to a coat protein of a bacteriophage, resulting in display of the fused protein on the exterior of the phage virion, while the DNA encoding the fusion resides within the virion. This physical linkage between the displayed protein and the DNA encoding it allows screening of vast numbers of variants of the protein, each linked to its corresponding DNA sequence, by a simple in vitro selection procedure called "biopanning".

Phage displayed antibody libraries have become a valuable tool for generating human antibodies or antibodies with selected specificities (Hogenboom, H. et al. 2000. *Immunology Today* 21(8), 371-378). Domain directed pannings have become a routine way of selecting antibodies that bind to a variety of epitopes on a target protein.

Ligand-capture directed panning is analogous to an ELISA sandwich assay in that an immobilized antibody to an irrelevant and non-adjacent epitope is used to capture and present the preferred binding face of the target ligand for phage panning (U.S. Pat. No. 6,376,170). Others have used competing antibodies to selectively mask the antigen at other than the desired target domain (Tsui, P. et al. 2002. J. Immunol. Meth. 263:123-132). Pathfinder technology uses a monoclonal and polyclonal antibodies, as well as natural ligands conjugated directly or indirectly to horseradish peroxidase (HRP). In the presence of biotin tyramine these molecules catalyze biotinylation of phage binding in close proximity to the target antigen, allowing specific recovery of 'tagged' phage from the total population using streptavidin. In this way, phage binding to the target itself, or in its immediate proximity, are selectively recovered (Osborn, J. K. et al. 1998. Immunotechnol. 3: 293-302). The use of monoclonal antibodies to direct binding to alternate sites has also been termed "epitope walking" (Osborn, J. K. et al. 1998. supra).

Such selections have primarily been achieved by employing a stepwise selection of antibodies. In the first stage of selection, a variety of antibodies are selected to the target protein. In the second stage of selection, panning is performed in the presence of one or more selected antibodies so that any newly selected antibodies must bind at a different epitope. The present invention employed a unique methodology that incorporates a hybrid human:murine TF competitor or decoy protein in the panning process to select antibodies that bind to the same regions as the 5G9 epitope. Several antibodies were selected that specifically interact with murine TF but not the hybrid protein and have properties similar to the parent anti-human TF antibody.

SUMMARY OF THE INVENTION

The present invention provides isolated anti-murine Tissue Factor antibodies, immunoglobulins, cleavage products and other specified portions and variants thereof, encoding or complementary nucleic acids, vectors, host cells, compositions and methods of making and using thereof, as described and enabled herein, in combination with what is known in the art. The antibodies of the invention bind murine tissue factor in one or more epitopes in the amino acid sequences of mTF that are in the same region as the epitope or epitopes to which the antibody 5G9 binds in human tissue factor and thus have biological properties similar to the 5G9 antibody. The murine antibodies of the invention are useful as research tools for evaluating the therapeutic potential of anti-tissue factor antibodies that neutralize TF activity by inhibiting the activation of Factor X and for exploring the role of TF in various biological processes.

The antibodies of the invention are useful as a surrogate in preclinical testing in murine hosts where the therapeutic candidate antibody for use in humans does not bind with the homolog murine target protein in a manner that would provide meaningful information about treatment efficacy or safety. The invention provides a method and an example of a method of selecting an antibody which is a true surrogate for use in pre-clinical testing of therapeutic biologic candidate in animal models, said method is based on the use of information about the three dimensional structure of the ligand binding site that imparts unique biological activity to the binding partner.

In one embodiment, the antibody binds to tissue factor receptor on the surface of a non-human cell and, prevents receptor-mediated events at the cell surface. In a preferred embodiment, the receptor is murine tissue factor on a murine cell and the antibody binding prevents the formation of an active ternary complex of TF:FVII:FX and thereby inhibits coagulation. In a particularly preferred embodiment, the antibody comprises a variable domain derived from MAb PHD126 or binding fragments thereof and inhibits coagulation, blocks cell-cell adhesion events, and prevents tumor cell growth and metastasis.

The invention also comprises the specific constructs for selecting the antibodies of the invention. Said constructs represent chimeric proteins insofar as substitutions are made in the protein of one species using the residues from a homolog protein of another species. In one embodiment of the invention, the chimeric protein is a murine tissue factor protein in which residues from human tissue factor have been substituted. In another embodiment the construct is a protein selected from the group consisting of SEQ ID NO: 3 or SEQ ID NO: 4.

The invention further comprises a method of selecting the antibody from a library of antibody variable regions using the chimeric protein as a decoy in a competitive biopanning step wherein the construct is in molar excess of the parent protein from which it was chimerized. In a particularly preferred embodiment of the method of the invention, a human antibody Fab library is panned for binders to murine TF in the presence of ten-fold molar excess of the purified protein of SEQ ID NO: 3.

BRIEF DESCRIPTION OF THE DRAWINGS

FIG. 1 shows schematic representations of the point at which tissue factor acts in the extrinsic pathway of the clotting cascade and the effect that blockage by the antibody TF8-5G9 has on the cascade.

FIG. 3 is a sequence alignment of human (SEQ ID NO: 1) and murine tissue factor (SEQ ID NO: 2) extracellular domain showing consensus sequence and with the TF8-5g9 binding domain of human TF and the homolog murine region outlined.

FIG. 4 is a table of the variable region sequences from the Fabs selected from a human antibody library using murine tissue factor and a decoy protein having SEQ ID NO: 3. The complete variable regions of each heavy and light chain is given in the sequence listing indicated.

DETAILED DESCRIPTION OF THE INVENTION

Figure 2:
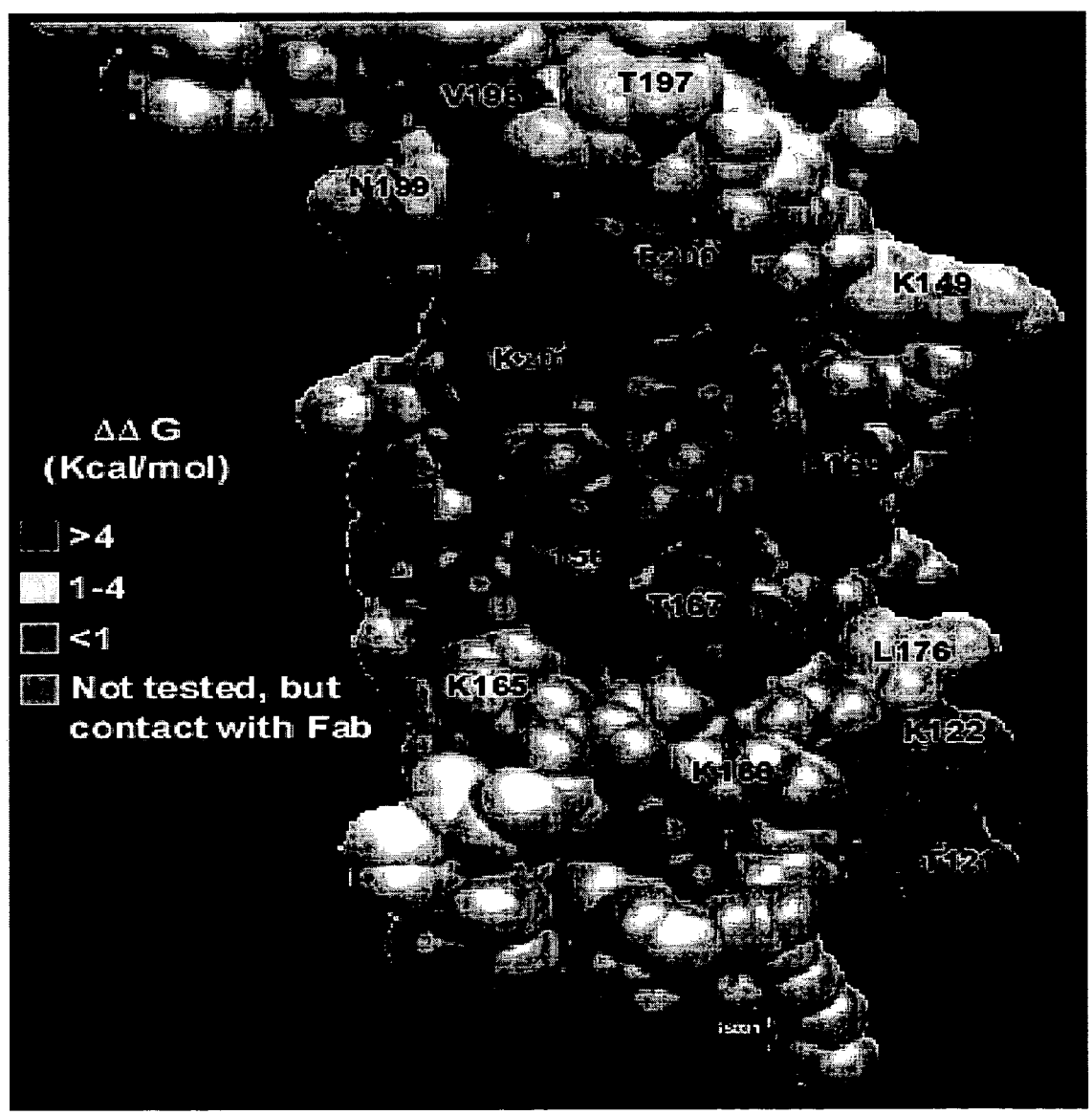
FIG. 2 is a representation of the three-dimensional structure of human tissue factor showing the residues and relative delta free energy of binding for residues involved with binding to Mab TF8-5G9 (from Huang et al. 1991).

The present invention provides isolated anti-murine Tissue Factor antibodies, immunoglobulins, cleavage products and other specified portions and variants thereof, encoding or complementary nucleic acids, vectors, host cells, compositions and methods of making and using thereof, as described and enabled herein, in combination with what is known in the art. The antibodies of the invention bind murine tissue factor in one or more epitopes in the amino acid sequences of mTF that are in the same region as the epitope or epitopes to which the antibody 5G9 binds in human tissue factor and thus have biological properties similar to the 5G9 antibody. The murine antibodies of the invention are useful as research tools for evaluating the therapeutic potential of anti-tissue factor antibodies that neutralize TF activity by inhibiting the activation of Factor X and for exploring the role of TF in various biological processes.

Using the crystal structure for the complex of human tissue factor and 5G9 (FIG. 2), residues that made a significant energetic contribution to the complex were identified. The sequences for human and murine tissue factor were then aligned and the residues critical for binding on the human protein were mapped to their analogous positions on the murine protein. Residues that were identical between the human and murine proteins were left unchanged while residues that were different on the mouse protein were mutated to the sequence for human tissue factor. In this way, a human-murine tissue factor hybrid protein was designed consisting predominantly of the murine tissue factor sequence with those residues predicted to interact with 5G9 corresponding to the human tissue factor sequence.

Panning experiments to identify epitope specific anti-tissue factor antibodies utilized murine tissue factor as the primary selection target with the human-murine hybrid tissue factor as a competitor. Addition of the hybrid competitor was used to minimize isolation of irrelevant antibodies and enrich the selection for antibodies that interact with murine tissue factor at the epitope recognized by 5G9. Selected antibodies were characterized in binding, coagulation, and FX enzymatic assays. These antibodies bind to murine cells expressed TF and competitively inhibit FX binding to the TF:FVII complex.

We have devised a method for epitope directed selection of phage-displayed antibodies using an engineered competitor protein. The method relies on structural information about the target protein to allow the design of an appropriate competitor. In addition, this method allows for the selection of antibodies reactive to specific epitopes on a protein of interest.

Existing methods of antibody selection using phage-displayed antibody libraries cannot be directed precisely to the epitope of interest. The disclosed method has the advantage of allowing very precise and effective direction of the selection toward antibodies specific for the targeted epitope. We have employed this method to allow selection of antibodies to a unique epitope on mTF. Existing antibodies in the art either do not inhibit mTF function or are not specific competitive inhibitors of Factor X binding to TF. The disclosed antibodies have these functions and therefore represent previously unavailable tools for evaluating the therapeutic potential for anti-TF antibodies that neutralize TF activity by inhibiting the activation of FX. In addition, these antibodies are valuable reagents for dissecting the role of TF in normal and pathogenic thrombotic inflammatory, angiogenic, neoplastic, and developmental processes.

Animal Models Useful for Pre-Clinical Testing

In pharmaceutical research, it has become commonplace to perform as efficacy as well as safety testing in animals as possible prior to subjecting human subjects to the dangers of exposure of a novel compound or biologic drug candidate. In the field of biopharmaceuticals, the human or "host" response to the test agent can include immune reaction to the protein which is an as yet unpredictable event, but also a myriad of other similarly complex effects. For example, while TNFalpha is capable of killing tumor cells in vitro, injection of TNFalpha into a living mammal precipitates a "cytokine storm" which can be lethal. Thus, it is important to understand not only the direct effects of therapy but the host response to it as well.

Commonly used animals for testing are mice, rats, guinea pigs, dogs, cynomolgous monkeys, and nonhuman primates. Some disease states have animal analogues either due to a natural or genetic defect. One example is the naturally obese and diabetic mouse genetically designated db/db. In other cases, models of disease can be induced in otherwise health animals; such as collagen-induced arthritis in mice or dextran induced inflammatory bowel disease. Although xenografts models have been developed whereby cells or tissues of one species are grafted into the bodies of another species, for example human tumor xenografts in mice, the host animal must be chemically or genetically immunosuppressed in order not to reject the tissue. Secondly, xenografts models may suffer from the complication that the target ligand is produced by the graft while its homolog protein is produced by the host.

While wishing to remain within humane guidelines and minimize the use and suffering brought to bear on any living entity, nonhuman testing as well as human testing is often necessary and indeed required for approval of new therapeutic products.

Biopharmaceuticals and, particularly, antibodies interact with a high degree of specificity on their targets as the interactive "face" is on the order of several hundred angstroms. For this reason, slight changes in the target, especially surface charge, can alter specificity and affinity of binding. Across species, especially within the family mammalae, there are many highly conserved protein structures and substructures or domain. However, antibodies to a protein from one species of mammal often do not recognize the protein from another species that performs the analogous role and may have considerable sequence identify if there are changes in the residues that form the binding face with that antibody.

For this reason, an expedient method of selecting a biologic surrogate which functions in a nonhuman animal in a manner as close a possible to the human therapeutic candidate would be of great utility. Having described the invention in general terms, it is further embodied by the following examples.

EXAMPLE 1

Design and Production of the Chimeric Human/Murine Tissue Factor Protein

The MAb designated TF8-5G9 recognizes and binds to human Tissue Factor and prevents association of Factor X with TF or the TF/Factor VIIa complex (Ruf, W. and Edgington, T. S. 1991.Thromb. Haemost. 66:529-539). Based on analysis of the crystal structure of the TF8-5G9 Fab complexed with human TF, all of the residues that form the epitope recognized by the Fab fall between residues 149 and 204 of human TF. This region of the protein is also known to play an important role in the interaction of TF with Gla-domain FX (Ruf et al 1992). Fifteen specific residues between 149 and 204 of human TF are located appropriately to make significant energetic contributions to binding (Huang, et al. *J. Mol. Biol.* 275, 873-894) (FIG. 2). The full sequence alignment between human (SEQ ID NO: 1) and murine tissue factor (SEQ ID NO: 2) is shown in FIG. 3. When the extracellular domain sequences of human (GenPept Accession No. NP_001984) and murine TF (GenPept Accession No. NP_034301) are aligned between residues 149 and 204 of the human EC domain and the 152-207 of the murine EC domain, seven of the fifteen significant residues are identical (human residues K149, K165, K166, T167, T170, N171, Q190) while eight of the fifteen residues are different (human residue replaced by: Y156T, K169I, V192M, P194F, V198T, R200Q, K201N and D204G). Residues in bold represent residues that contribute significantly to stabilization of TF8-5G9:huTF complex. These residues have a delta free energy of binding of 1-4 kcal/mol or greater.

```
Human
 149KDLIYTLYYWKSSSSGKKTAKTNTNEFLIDVDKGENYCFSVQAVIPS

RTVNRKSTD204
(SEQ ID NO:15)

Mouse
 152KDLGYIITYRKGSSTGKKTNITNTNERSIDVEEGVSYCFFVQAMIFS

RKTNQNSPG207
(SEQ ID NO: 16)
```

According to this analysis, a chimeric protein decoy protein could be constructed from the murine Tissue Factor coding sequence making mutations of the unique TF8-5G9 contact residues on mTF to correspond to the residue found on huTF at the position according to the alignment. Although there are other positions where there are amino acid residue differences between murine and human tissue factor, these were assumed not to contribute to the overall function or structure of the protein in terms of the targeted epitope. Using the mTF gene as a template, a chimeric protein was constructed having mutations of the eight unique TF8-5G9 contact residues on mTF to the corresponding residue found on huTF (SEQ ID NO. 3). The membrane-spanning region was deleted so that only the soluble extracellular domain of TF was expressed and a carboxy-terminal His-tag was added to simplify purification. The soluble murine TF and the chimeric protein were expressed and purified from HEK 293E cells. Purified protein was analyzed by SDS-PAGE to show the expected MW for Hu/m TF (40 kDa) and for mTF (35 Kda).

EXAMPLE 2

Use of Chimeric Murine:Human Tissue Factor as a Decoy in Competitive Biopanning for Antibodies Binding to a Preseleted Epitope Solution based panning with the HuCAL phage display library (Morphosys, Martinsried, Germany) was accomplished using biotinylated mTF protein. Chimeric hu/mTF protein was added as a decoy at a ten-fold molar excess to de-select phage specific for all epitopes except for the targeted epitope on mTF. Phage bound to biotinylated mTF were recovered by capture on streptavidin coated magnetic beads. All binders were sequenced to yield twenty-three unique Fabs from this panning: at the concentration tested, 9 recognized only mTF, 3 preferentially recognized mTF over hu/mTF, and 11 recognized the two proteins similarly (Table 1).

A panning on mTF without the chimeric protein competitor was performed to verify that the Fabs selected were the result of the epitope directed selection and not a hotspot on mTF. Panning conditions were identical between the two experiments except for the omission of the competing antigen in the selection process. All binders were sequenced to yield seven unique Fabs. Only one of the Fabs isolated in the panning without competitor bound specifically to mTF suggesting that addition of the competitor antigen allowed selection of Fabs that specifically recognize mTF and not the hu/mTF protein with changes in the TF8-5G9 epitope.

TABLE 1

| Panning Experiment | Fab Clones Binding | | |
|---|---|---|---|
| | mTF >> h/mTF | mTF > hu/mTF | mTF = h/mTF |
| Competition (m/hTG = 10X mTF) | 9/23 | 3/23 | 11/23 |
| mTF only | 1/7 | 2/7 | 4/7 |

Figure 5:
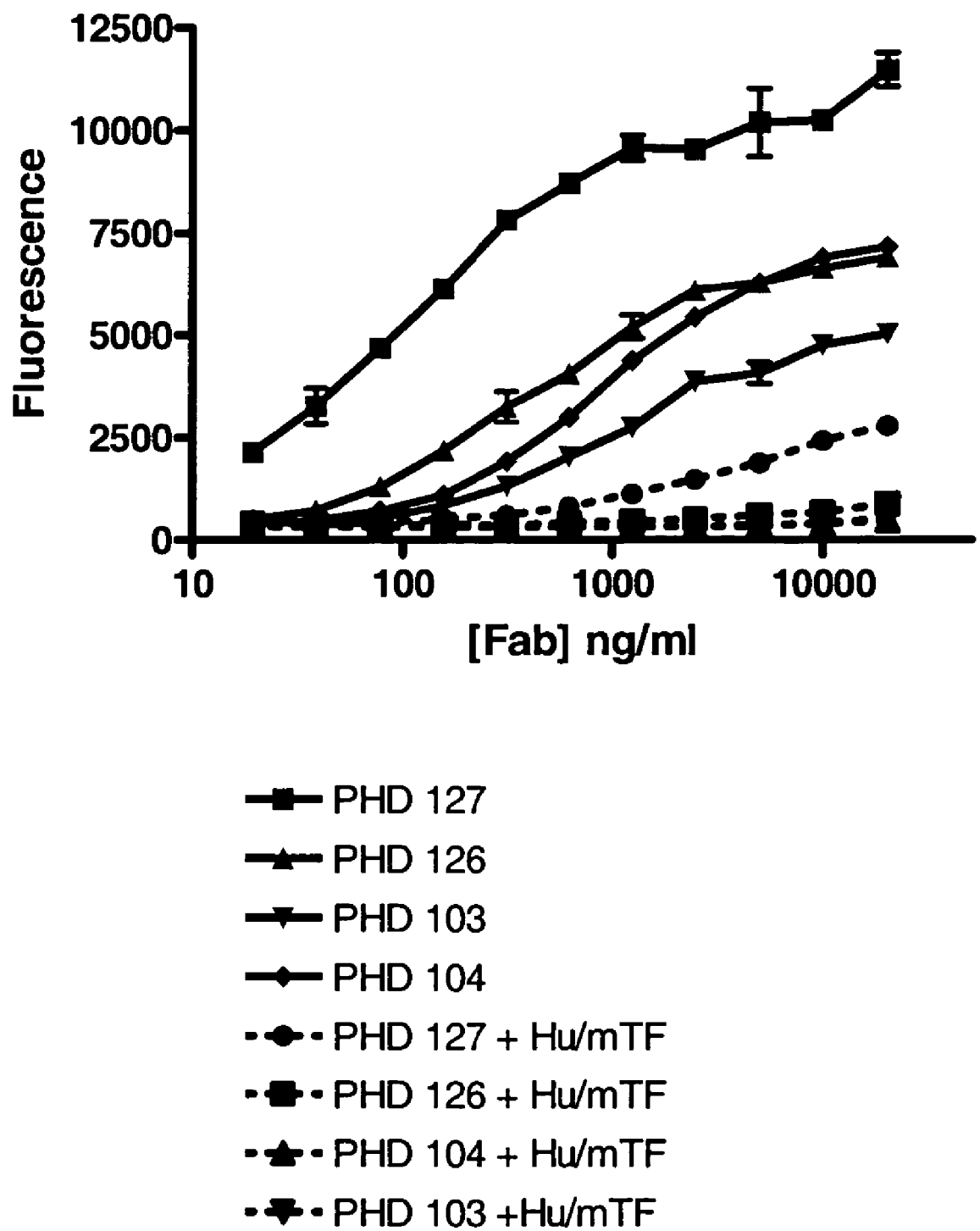
FIG. 5 is a binding assay of the Fabs selected showing binding to the target protein, native murine TF (SEQ ID NO: 2), versus binding to the decoy protein murine:human TF having SEQ ID NO: 3.

Human anti-murine TF specific Fabs were purified by affinity chromatography and evaluated for binding to mTF or hu/mTF by ELISA. All nine mTF specific Fabs demonstrated dose dependent binding to mTF with minimal cross reactivity to the hu/mTF (FIG. 5). In this format, PHD127 had the highest binding affinity for mTF in this format while PHD103 had the lowest. The CDR sequences for these Fabs are listed in FIG. 4; framework assignments were made by comparison to the Morphosys HuCAL manual. Framework sequences are listed in the lower section of FIG. 4. The variable regions of the heavy and light chains for the five Fabs (PHD 103, 104, 126, 127, and 130) as shown by individual subdomain components in FIG. 4 are included at SEQ ID NOS: 5-14, respectively. These variable domains were cloned into vectors for expression of mIgG2a molecules in HEK 293 cells. Five Fabs (PHD 103, 104, 126, 127, and 130) were selected for conversion into full-length immunoglobulins based on their affinity for mTF.

Inhibition of Coagulation

The selected anti-mTF surrogate Fabs were evaluated for their ability to inhibit coagulation in human plasma using murine brain extracts as a source of mTF. Based on previous experiments, Fabs that bind to the TF8-5G9 epitope on mTF are expected to interrupt the coagulation pathway and delay clot formation. In this assay, inhibition of fibrin clot formation was measured in human plasma. Four of the eight Fabs tested delayed or inhibited coagulation in human plasma in vitro: PHD 103, PHD 104, PHD 126 and PHD 127. PHD126 and PHD 127 were significantly more potent at inhibiting coagulation in human plasma. Based on the curve fit to the clotting time versus Fab concentration the measurable E50 values ranged from 0.2 μg/ml to 63 μg/ml.

TABLE 2

| Fab | EC50 Conc. (ug/ml) for human plasma | Time to Clot murine Plasma (sec) |
|---|---|---|
| PHD102 | >200 | 68 |
| PHD103 | 63.3 | ND |
| PHD104 | 23.8 | ND |
| PHD109 | >200 | ND |
| PHD126 | 0.23 | 102 |
| PHD127 | 0.82 | 172 |
| PHD128 | >200 | 74 |
| PHD129 | >200 | 58 |

Some of the mTF surrogate Fabs were then evaluated for their ability to inhibit coagulation in a clotting assay. Any Fab that binds to the TF8-5G9 epitope of mTF is expected to interrupt the coagulation pathway. Vials containing equal volumes of murine plasma (Lampire Biologics) and HuTF (Oregon Teknika catalog #59847) were treated with either Fabs (200, 50, 12.5,3.1 mg/ml) or HBSS (Ca—/Mg—). Initiation of clot formation was recorded manually with a timer. All samples were analyzed in duplicate at 37° C. The average time to fibrin clot formation in the presence of 50 microgm/ml of each Fab is given in Table 2. PHD 126 and PHD 127 delayed clot formation the longest when compared to mock treated plasma at all concentrations.

Factor X Inhibition

Factor X inhibition by those anti-mTF Fabs that inhibited coagulation (PHD 103, 104, 126, 127) was measured in the presence of murine brain extracts (as the source of tissue factor). Extracts were incubated with FVIIa, and anti-mTF surrogate Mabs were added in the presence of FX and inhibition of the conversion of FX to FXa was measured. PHD 103, 126 & 127 Fabs inhibited Factor X activation (cleavage) to Factor Xa. Inhibition of Factor X activation was subsequently reevaluated using the full-length anti-mTF IgGs. Good inhibition was observed for PHD 103, 126 and 127, while no inhibition was observed with PHD 104.

FACS Analysis

Figure 6:
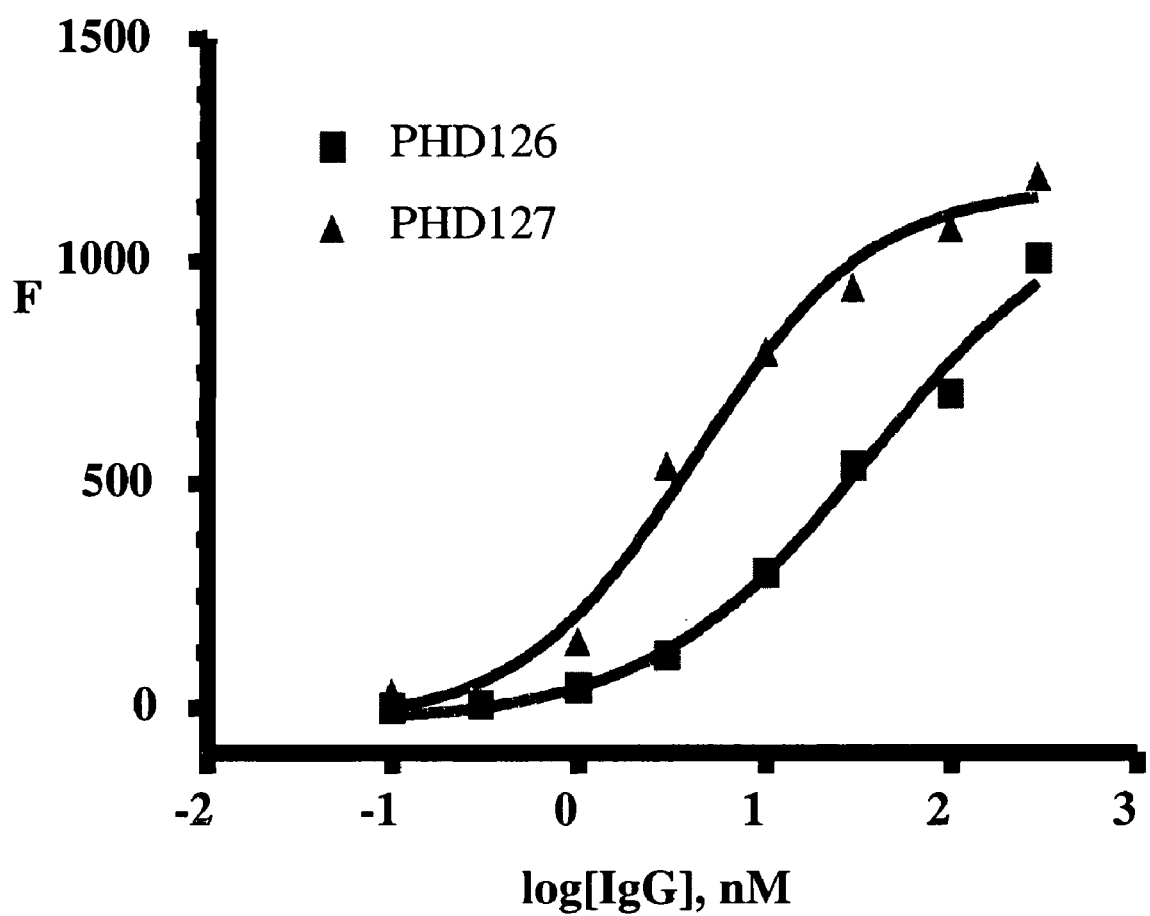
FIG. 6 is graph of the concentration versus relative fluorescence of cells expressing mTF on the surface and bound by two FAbs selected by the method of the invention.

As the most active attractive candidate antibodies, PHD126 and PHD127 were evaluated for their ability to bind to B6F10 melanoma cells that express mTF at high levels. PHD126 and PHD127 bound cell-associated mTF in a dose dependent manner with an EC50 of 37.8 nM or 4.35 nM respectively (FIG. 6).

SUMMARY

The experiments described herein demonstrate that epitope directed selection of phage-displayed antibodies using an engineered competitor protein is a viable process. The method relies on structural information about the target protein to allow the design of an appropriate competitor. In addition, this method allows for the selection of antibodies reactive to specific epitopes on a protein of interest. Existing methods of antibody selection using phage-displayed antibody libraries cannot be directed precisely to the epitope of interest. The disclosed method has the advantage of allowing very precise and effective direction of the selection toward antibodies specific for the targeted epitope. We have employed this method to allow selection of antibodies to a unique epitope on mTF.

TF is a complex molecule which functions both as a receptor and as an ligand, being capable of forming a unique complex with FVIIa and FX. Thus, Mabs that prevent this interaction must be directed to a unique region of the molecule. Existing antibodies in the art either do not inhibit mTF function or are not specific competitive inhibitors of Factor X binding to TF. The disclosed antibodies have these functions and therefore represent previously unavailable tools for evaluating the therapeutic potential for anti-TF antibodies that neutralize TF activity by inhibiting the activation of FX. In addition, these antibodies are valuable reagents for dissecting the role of TF in normal and pathogenic thrombotic inflammatory, angiogenic, neoplastic, and developmental processes.

EXAMPLE 3

Contribution of Host Effector Function

Evaluation of anti-tissue factor combination therapy using CDR graphed variable domains based on TF8-5G9 (as taught in applicants co-pending applications WO 96/40921 and U.S. Ser. No. 11/010797) and fused to a human IgG1 constant region (CNTO 860) and the mouse surrogate antibody, PHD 126, in the orthotopic human breast carcinoma MDA MB 231 xenograft model in SCID Beige mice is described.

PHD 126 Fab was converted to a full-length murine antibody with effector function by fusing the human anti-murine TF variable region to a murine IgG2a heavy chain constant region. Similar to human isotypes, murine antibodies have also been characterized for their ability to induce various effector functions such as ADCC, and complement mediated cytotoxicity. For example, murine macrophages are reportedly able to interact with mouse IgG2a antibodies to promote tumor cell killing (Johnson et a. 1985. Adv Exp Med Biol 1985; 184:75-80).

As PHD 126 recognizes murine tissue factor, it has the potential to react with the mouse vasculature and other murine components expressing TF (e.g. activated monocytes) whereas CNTO 860 targets the implanted human MDA MB 231 tumor cells.

Other test antibodies are an irrelevant human isotype-matched control antibody, F105, and the PDH 126 isotypic counterpart, cVaM.

Female SCID Beige mice (C.B-17/IcrCrI-scid-bgBR) approximately 18-20 g in weight were obtained from Charles River Laboratories and acclimated for 10-14 days prior to experimentation. For the study 24 mice were assigned to 4 groups, 6 animals per group. On day 0, $2.5 \times 10^6$ cells were implanted into the mammary fat pad (#2 or # right inguinal fat pad) of SCID/Beige mice in 50 uL PBS. Once-weekly therapy commenced 3 days post tumor cell implantation using either PBS injections or the test and control antibodies in the combinations shown in and times given in Table 3. Animal weights and tumor volumes were monitored starting on day 3 and once weekly thereafter for 8 weeks. Tumor volumes were calculated as $(L \times W^2)/2$. Primary tumors were surgically removed, weighed and fixed in BZF solution.

TABLE 3

| Group | N | Antibodies Given | Day 3 Initiation, Dose Given | Schedule × 8 weeks |
|---|---|---|---|---|
| 1 | 6 | CVaM | 5 mg/kg | 2 × week |
|   |   | F105 | 0.03 mg/kg | 1 × week |
| 2 | 6 | PHD 126 | 5 mg/kg | 2 × week |
|   |   | F105 | 0.03 mg/kg | 1 × week |
| 3 | 6 | CVaM | 5 mg/kg | 2 × week |
|   |   | CNTO 860 | 0.03 mg/kg | 1 × week |
| 4 | 6 | PHD 126 | 5 mg/kg | 2 × week |
|   |   | CNTO 860 | 0.03 mg/kg | 1 × week |

Figure 7:
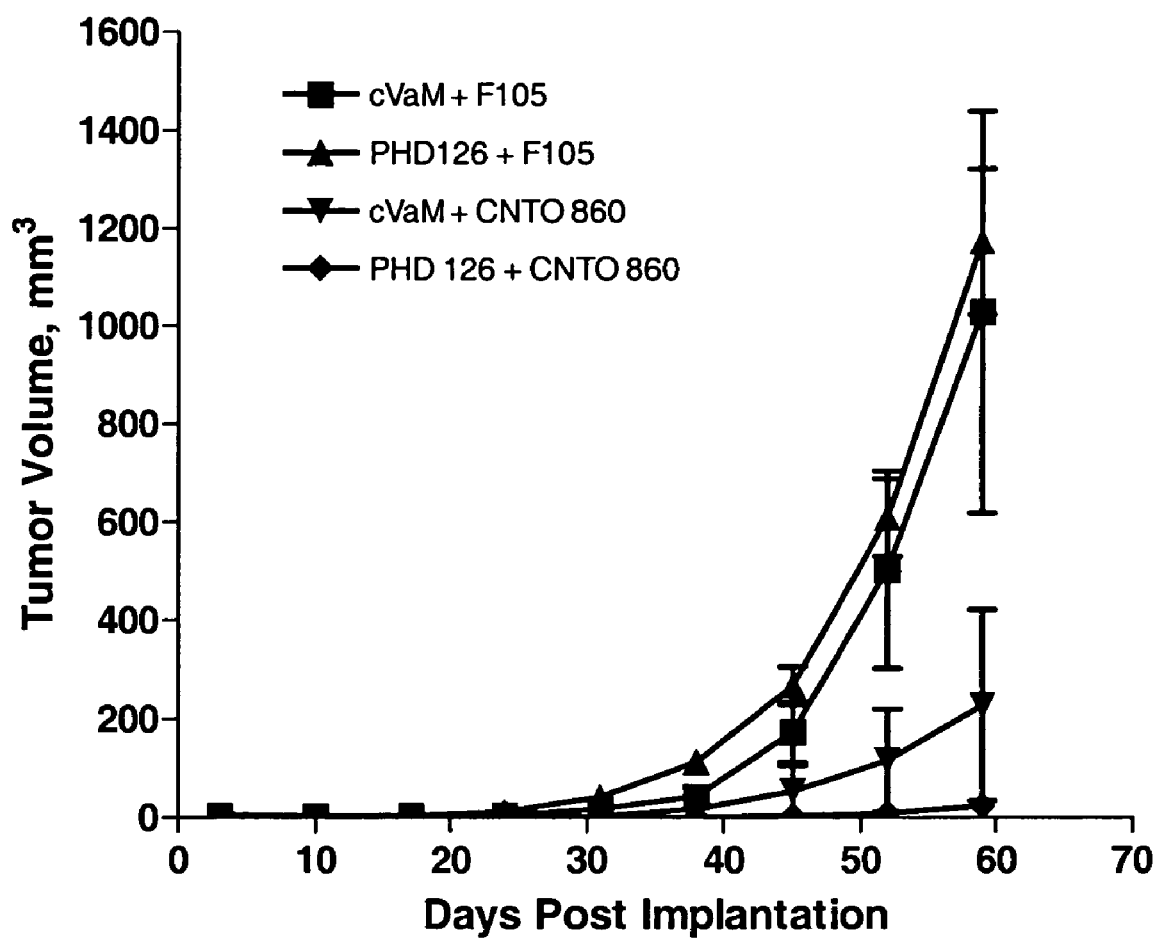
FIG. 7 is graph showing human breast tumor cell (MDA MB-231) growth over time in SCID beige mice treated with anti-human tissue factor (CNTO 860) plus the anti-mouse tissue factor (PHD 126 IgG2a version) both of which are of isotypes capable of eliciting effector functions for the respective species. F105 and cVam are isotype matched control antibodies. Antibody injections were given once per week for 8 weeks.
Figure 8:
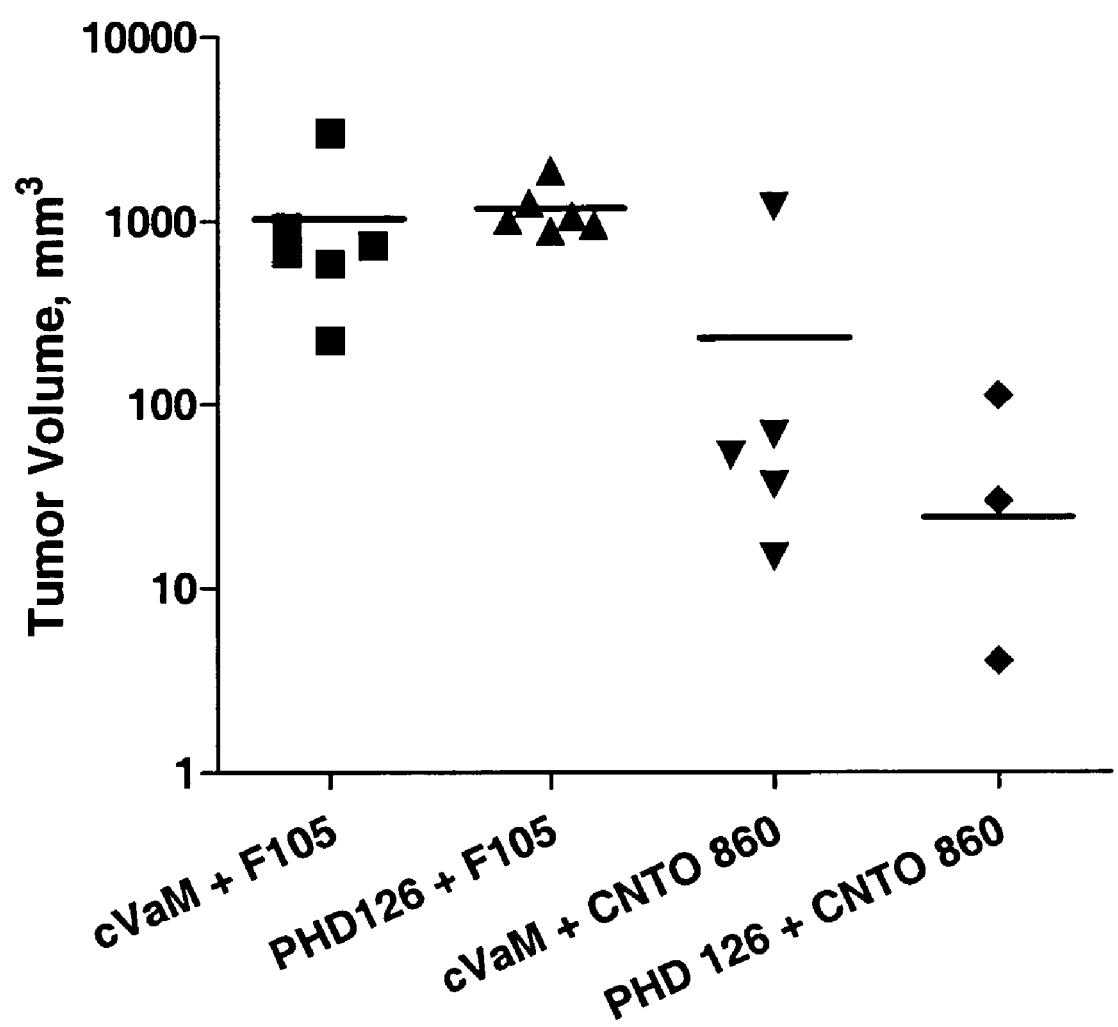
FIG. 8 is scatter plot of the individual final tumor masses for the experiment as described for FIG. 7.
Figure 9:
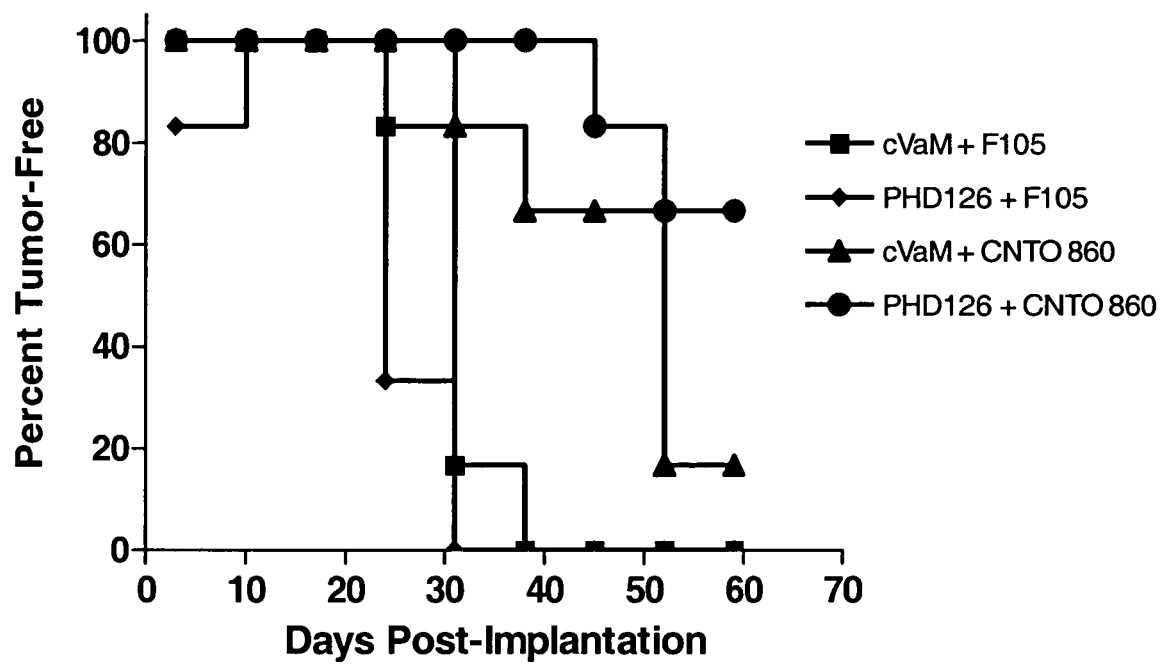
FIG. 9 is a plot of the percent of tumor free mice by group over time in the experiment as described for FIG. 7.

FIGS. 7-9 show the results of this experiment. CNTO 860, targeting only TF on the implanted tumor cells, was intentionally dosed at a partially effective dose of 0.03 mg/kg. FIG. 7 shows that treatment with this dose of CNTO 860 combined with the inactive control mouse IgG, cVaM, resulted in substantial but incomplete inhibition of tumor growth relative to the inactive cVaM+F105 control treatment group (77% reduction, p=0.0078, t-test). Treatment with PHD 126+F105, targeting only host TF on tumor stromal and endothelial cells, did not affect tumor inhibition in this model, as shown in FIG. 8.

The results of this study suggests that targeting TF only on tumor endothelial and stromal cells is insufficient to inhibit tumor growth in this model. However, combining CNTO 860 and PHD 126 in a regimen that targets both tumor cell TF and stromal TF results in improved tumor control relative to each therapy alone, as illustrated by the nearly complete suppression of tumor growth by the endpoint of the study (FIG. 8). Combination therapy with CNTO 860+PHD 126 inhibited tumor growth by 97% compared to the control group (p=0.0039, t-test), by 90% relative to CNTO 860 monotherapy (p=0.0391) and by 98% versus PHD 126 monotherapy alone (p=0.0039, t-test). This interaction is, in fact, synergistic based on the observation that PHD 126 alone produced 0% inhibition but adds anti-tumor efficacy in combination. FIG. 8 shows the results of the experiment in the form of a scatter-plot of final tumor volumes and confirms the conclusions drawn from the inhibition of tumor development and growth between the treatment groups (FIG. 7).

FIG. 9 graphically represents that CNTO 860 administration results in a delay of onset of measurable tumors but anti-murine TF (PHD 126) alone does not. The combination of CNTO 860 and PHD 126, targeting both tumor and host TF, results in a further delay of tumor onset and significantly reduces the incidence of tumor growth at the end of the study as compared to either agent alone. These results confirm the synergistic anti-tumor effects of targeting TF on both tumor cells and host stromal cells. Thus for the first time, it was demonstrated that targeting TF in the host tumor stroma with a monoclonal antibody provides an anti-tumor benefit.

The invention claimed is:

1. An isolated monoclonal antibody which binds tissue factor comprising an amino acid sequence selected from at least one of SEQ ID NOS: 5-14.

2. The monoclonal antibody of claim 1, wherein the antibody comprises heavy chain CDR1 sequence of SEQ. ID. NO: 9 from residue 26 to 34 inclusive, a heavy chain CDR2 sequence of SEQ. ID. NO: 9 from residue 49 to 65 inclusive, and a heavy chain CDR3 sequence of SEQ. ID. NO: 9 from residue 98 to 108 inclusive; and a light chain CDR1 sequence of SEQ ID NO: 10 from residue 23 to 33 inclusive, a light chain CDR2 sequence of SEQ ID NO: 10 from residue 49 to 55 inclusive, and a light chain CDR3 sequence of SEQ ID NO: 10 from residue 88 to 97 inclusive.

3. The monoclonal antibody of claim 1, wherein the antibody comprises a heavy chain CDR 1 sequence of SEQ. ID. NO: 11 from residue 26 to 34 inclusive, a heavy chain CDR2 sequence of SEQ ID NO: 11 from residue 49 to 65 inclusive, and a heavy chain CDR3 sequence of SEQ ID NO: 11 from residue 98 to 108 inclusive; and a light chain CDR1 sequence of SEQ ID NO: 12 from residue 23 to 33 inclusive, a light chain CDR2 sequence of SEQ ID NO: 12 from residue 49 to 55 inclusive, and a light chain CDR3 sequence of SEQ ID NO: 12 from residue 88 to 96 inclusive.

* * * * *

SEQUENCE LISTING

```
<160> NUMBER OF SEQ ID NOS: 14

<210> SEQ ID NO 1
<211> LENGTH: 219
<212> TYPE: PRT
<213> ORGANISM: Homo sapiens
<220> FEATURE:
<221> NAME/KEY: BINDING
<222> LOCATION: (149)..(204)
<223> OTHER INFORMATION: 149, 156, 165-167, 169-171, 190, 192, 198,
      200-201, 204
<220> FEATURE:
<221> NAME/KEY: BINDING
<222> LOCATION: (149)..(204)

<400> SEQUENCE: 1

Ser Gly Thr Thr Asn Thr Val Ala Ala Tyr Asn Leu Thr Trp Lys Ser
1               5                   10                  15

Thr Asn Phe Lys Thr Ile Leu Glu Trp Glu Pro Lys Pro Val Asn Gln
```

-continued

```
                    20                  25                  30
Val Tyr Thr Val Gln Ile Ser Thr Lys Ser Gly Asp Trp Lys Ser Lys
                35                  40                  45

Cys Phe Tyr Thr Thr Asp Thr Glu Cys Asp Leu Thr Asp Glu Ile Val
 50                  55                  60

Lys Asp Val Lys Gln Thr Tyr Leu Ala Arg Val Phe Ser Tyr Pro Ala
 65                  70                  75                  80

Gly Asn Val Glu Ser Thr Gly Ser Ala Gly Glu Pro Leu Tyr Glu Asn
                 85                  90                  95

Ser Pro Glu Phe Thr Pro Tyr Leu Glu Thr Asn Leu Gly Gln Pro Thr
                100                 105                 110

Ile Gln Ser Phe Glu Gln Val Gly Thr Lys Val Asn Val Thr Val Glu
                115                 120                 125

Asp Glu Arg Thr Leu Val Arg Arg Asn Asn Thr Phe Leu Ser Leu Arg
                130                 135                 140

Asp Val Phe Gly Lys Asp Leu Ile Tyr Thr Leu Tyr Tyr Trp Lys Ser
145                 150                 155                 160

Ser Ser Ser Gly Lys Lys Thr Ala Lys Thr Asn Thr Asn Glu Phe Leu
                165                 170                 175

Ile Asp Val Asp Lys Gly Glu Asn Tyr Cys Phe Ser Val Gln Ala Val
                180                 185                 190

Ile Pro Ser Arg Thr Val Asn Arg Lys Ser Thr Asp Ser Pro Val Glu
                195                 200                 205

Cys Met Gly Gln Glu Lys Gly Glu Phe Arg Glu
                210                 215
```

<210> SEQ ID NO 2
<211> LENGTH: 221
<212> TYPE: PRT
<213> ORGANISM: Mus sp.
<220> FEATURE:
<221> NAME/KEY: BINDING
<222> LOCATION: (152)..(207)

<400> SEQUENCE: 2

```
Gly Ile Pro Glu Lys Ala Phe Asn Leu Thr Trp Ile Ser Thr Asp Phe
 1               5                  10                  15

Lys Thr Ile Leu Glu Trp Gln Pro Lys Pro Thr Asn Tyr Thr Tyr Thr
                20                  25                  30

Val Gln Ile Ser Asp Arg Ser Arg Asn Trp Lys Asn Lys Cys Phe Ser
                35                  40                  45

Thr Thr Asp Thr Glu Cys Asp Leu Thr Asp Glu Ile Val Lys Asp Val
 50                  55                  60

Thr Trp Ala Tyr Glu Ala Lys Val Leu Ser Val Pro Arg Arg Asn Ser
 65                  70                  75                  80

Val His Gly Asp Gly Asp Gln Leu Val Ile His Gly Glu Glu Pro Pro
                 85                  90                  95

Phe Thr Asn Ala Pro Lys Phe Leu Pro Tyr Arg Asp Thr Asn Leu Gly
                100                 105                 110

Gln Pro Val Ile Gln Gln Phe Glu Gln Asn Gly Arg Lys Leu Asn Val
                115                 120                 125

Val Val Lys Asp Ser Leu Thr Leu Val Arg Lys Asn Gly Thr Phe Leu
                130                 135                 140

Thr Leu Arg Gln Val Phe Gly Lys Asp Leu Gly Tyr Ile Ile Thr Tyr
145                 150                 155                 160
```

```
Arg Lys Gly Ser Ser Thr Gly Lys Lys Thr Asn Ile Thr Asn Thr Asn
            165                 170                 175

Glu Phe Ser Ile Asp Val Glu Gly Val Ser Tyr Cys Phe Phe Val
            180                 185                 190

Gln Ala Met Ile Phe Ser Arg Lys Thr Asn Gln Asn Ser Pro Gly Ser
            195                 200                 205

Ser Thr Val Cys Thr Glu Gln Trp Lys Ser Phe Leu Gly
            210                 215                 220
```

<210> SEQ ID NO 3
<211> LENGTH: 221
<212> TYPE: PRT
<213> ORGANISM: Artificial Sequence
<220> FEATURE:
<223> OTHER INFORMATION: Murine TF grafted with 8 murine residues

<400> SEQUENCE: 3

```
Gly Ile Pro Glu Lys Ala Phe Asn Leu Thr Trp Ile Ser Thr Asp Phe
1               5                   10                  15

Lys Thr Ile Leu Glu Trp Gln Pro Lys Pro Thr Asn Tyr Thr Tyr Thr
            20                  25                  30

Val Gln Ile Ser Asp Arg Ser Arg Asn Trp Lys Asn Lys Cys Phe Ser
            35                  40                  45

Thr Thr Asp Thr Glu Cys Asp Leu Thr Asp Glu Ile Val Lys Asp Val
        50                  55                  60

Thr Trp Ala Tyr Glu Ala Lys Val Leu Ser Val Pro Arg Arg Asn Ser
65                  70                  75                  80

Val His Gly Asp Gly Asp Gln Leu Val Ile His Gly Glu Glu Pro Pro
                85                  90                  95

Phe Thr Asn Ala Pro Lys Phe Leu Pro Tyr Arg Asp Thr Asn Leu Gly
            100                 105                 110

Gln Pro Val Ile Gln Gln Phe Glu Gln Asn Gly Arg Lys Leu Asn Val
            115                 120                 125

Val Val Lys Asp Ser Leu Thr Leu Val Arg Lys Asn Gly Thr Phe Leu
        130                 135                 140

Thr Leu Arg Gln Val Phe Gly Lys Asp Leu Gly Tyr Ile Ile Tyr Tyr
145                 150                 155                 160

Arg Lys Gly Ser Ser Thr Gly Lys Lys Thr Asn Lys Thr Asn Thr Asn
                165                 170                 175

Glu Phe Ser Ile Asp Val Glu Gly Val Ser Tyr Cys Phe Phe Val
            180                 185                 190

Gln Ala Val Ile Pro Ser Arg Lys Val Asn Arg Lys Ser Pro Asp Ser
            195                 200                 205

Ser Thr Val Cys Thr Glu Gln Trp Lys Ser Phe Leu Gly
            210                 215                 220
```

<210> SEQ ID NO 4
<211> LENGTH: 219
<212> TYPE: PRT
<213> ORGANISM: Artificial Sequence
<220> FEATURE:
<223> OTHER INFORMATION: Human TF grafted with 8 murine residues

<400> SEQUENCE: 4

```
Ser Gly Thr Thr Asn Thr Val Ala Ala Tyr Asn Leu Thr Trp Lys Ser
1               5                   10                  15

Thr Asn Phe Lys Thr Ile Leu Glu Trp Glu Pro Lys Pro Val Asn Gln
            20                  25                  30
```

```
Val Tyr Thr Val Gln Ile Ser Thr Lys Ser Gly Asp Trp Lys Ser Lys
            35                  40                  45

Cys Phe Tyr Thr Thr Asp Thr Glu Cys Asp Leu Thr Asp Glu Ile Val
 50                  55                  60

Lys Asp Val Lys Gln Thr Tyr Leu Ala Arg Val Phe Ser Tyr Pro Ala
 65                  70                  75                  80

Gly Asn Val Glu Ser Thr Gly Ser Ala Gly Glu Pro Leu Tyr Glu Asn
                 85                  90                  95

Ser Pro Glu Phe Thr Pro Tyr Leu Glu Thr Asn Leu Gly Gln Pro Thr
                100                 105                 110

Ile Gln Ser Phe Glu Gln Val Gly Thr Lys Val Asn Val Thr Val Glu
            115                 120                 125

Asp Glu Arg Thr Leu Val Arg Arg Asn Asn Thr Phe Leu Ser Leu Arg
130                 135                 140

Asp Val Phe Gly Lys Asp Leu Ile Tyr Ile Leu Thr Tyr Trp Lys Ser
145                 150                 155                 160

Ser Ser Ser Gly Lys Lys Thr Asn Ile Thr Asn Thr Asn Glu Phe Leu
                165                 170                 175

Ile Asp Val Asp Lys Gly Glu Asn Tyr Cys Phe Ser Val Gln Ala Val
            180                 185                 190

Ile Pro Ser Arg Thr Thr Asn Gln Asn Ser Thr Gly Ser Pro Val Glu
            195                 200                 205

Cys Met Gly Gln Glu Lys Gly Glu Phe Arg Glu
            210                 215

<210> SEQ ID NO 5
<211> LENGTH: 118
<212> TYPE: PRT
<213> ORGANISM: Human
<220> FEATURE:
<221> NAME/KEY: BINDING
<222> LOCATION: (26)..(35)
<223> OTHER INFORMATION: CDR1
<220> FEATURE:
<221> NAME/KEY: BINDING
<222> LOCATION: (50)..(67)
<223> OTHER INFORMATION: CDR2
<220> FEATURE:
<221> NAME/KEY: BINDING
<222> LOCATION: (100)..(107)
<223> OTHER INFORMATION: CDR3

<400> SEQUENCE: 5

Gln Val Gln Leu Val Gln Ser Gly Ala Glu Val Lys Lys Pro Gly Glu
 1               5                  10                  15

Ser Leu Lys Ile Ser Cys Lys Gly Ser Gly Tyr Ser Phe Ser Asn Ser
             20                  25                  30

Trp Ile Ala Trp Val Arg Gln Met Pro Gly Lys Gly Leu Glu Trp Met
         35                  40                  45

Gly Gly Ile Ile Gly Pro Gly His Ser Tyr Thr Lys Tyr Ser Pro Ser
     50                  55                  60

Phe Gln Gly Gln Val Thr Ile Ser Ala Asp Lys Ser Ile Ser Thr Ala
 65                  70                  75                  80

Tyr Leu Gln Trp Ser Ser Leu Lys Ala Ser Asp Thr Ala Met Tyr Tyr
                 85                  90                  95

Cys Ala Arg Ile Asn Met Gly Tyr Phe Asp Tyr Trp Gly Gln Gly Thr
            100                 105                 110

Leu Val Thr Val Ser Ser
```

115

<210> SEQ ID NO 6
<211> LENGTH: 111
<212> TYPE: PRT
<213> ORGANISM: Human
<220> FEATURE:
<221> NAME/KEY: BINDING
<222> LOCATION: (23)..(34)
<223> OTHER INFORMATION: CDR1
<220> FEATURE:
<221> NAME/KEY: BINDING
<222> LOCATION: (50)..(56)
<223> OTHER INFORMATION: CDR2
<220> FEATURE:
<221> NAME/KEY: BINDING
<222> LOCATION: (89)..(99)
<223> OTHER INFORMATION: CDR3

<400> SEQUENCE: 6

Asp Ile Glu Leu Thr Gln Pro Pro Ser Val Ser Val Ala Pro Gly Gln
1               5                   10                  15

Thr Ala Arg Ile Ser Cys Ser Gly Asp Ser Leu Gly Leu Lys Lys Phe
            20                  25                  30

Val Ser Trp Tyr Gln Gln Lys Pro Gly Gln Ala Pro Val Leu Val Ile
        35                  40                  45

Tyr Asp Asp Ser Asn Arg Pro Ser Gly Ile Pro Glu Arg Phe Ser Gly
50                  55                  60

Ser Asn Ser Gly Asn Thr Ala Thr Leu Thr Ile Ser Gly Thr Gln Ala
65                  70                  75                  80

Glu Asp Glu Ala Asp Tyr Tyr Cys Gly Thr Tyr Asp Gln Thr Ile Gly
                85                  90                  95

His Asp Val Val Phe Gly Gly Gly Thr Lys Leu Thr Val Leu Gly
            100                 105                 110

<210> SEQ ID NO 7
<211> LENGTH: 116
<212> TYPE: PRT
<213> ORGANISM: Human
<220> FEATURE:
<221> NAME/KEY: BINDING
<222> LOCATION: (26)..(34)
<223> OTHER INFORMATION: CDR1
<220> FEATURE:
<221> NAME/KEY: BINDING
<222> LOCATION: (49)..(65)
<223> OTHER INFORMATION: CDR2
<220> FEATURE:
<221> NAME/KEY: BINDING
<222> LOCATION: (98)..(105)
<223> OTHER INFORMATION: CDR3

<400> SEQUENCE: 7

Gln Val Gln Leu Val Gln Ser Gly Ala Glu Val Lys Lys Pro Gly Glu
1               5                   10                  15

Ser Leu Lys Ile Ser Cys Lys Gly Ser Tyr Ser Phe Thr Ser Asn Trp
            20                  25                  30

Ile Gly Trp Val Arg Gln Met Pro Gly Lys Gly Leu Glu Trp Met Gly
        35                  40                  45

Trp Ile Tyr Pro Ser Asp Ser Met Thr Arg Tyr Ser Pro Ser Phe Gln
50                  55                  60

Gly Gln Val Thr Ile Ser Ala Asp Lys Ser Ile Ser Thr Ala Tyr Leu
65                  70                  75                  80

Gln Trp Ser Ser Leu Lys Ala Ser Asp Thr Ala Met Tyr Tyr Cys Ala

-continued

```
                85                  90                  95
Arg Tyr Leu Phe Gly Leu Phe Asp Asn Trp Gly Gln Gly Thr Leu Val
            100                 105                 110

Thr Val Ser Ser
        115

<210> SEQ ID NO 8
<211> LENGTH: 107
<212> TYPE: PRT
<213> ORGANISM: Human
<220> FEATURE:
<221> NAME/KEY: BINDING
<222> LOCATION: (23)..(33)
<223> OTHER INFORMATION: CDR1
<220> FEATURE:
<221> NAME/KEY: BINDING
<222> LOCATION: (49)..(55)
<223> OTHER INFORMATION: CDR2
<220> FEATURE:
<221> NAME/KEY: BINDING
<222> LOCATION: (88)..(95)
<223> OTHER INFORMATION: CDR3

<400> SEQUENCE: 8

Asp Ile Glu Leu Thr Gln Pro Pro Ser Val Ser Val Ala Pro Gly Gln
1               5                   10                  15

Thr Ala Arg Ile Ser Cys Ser Gly Asp Asn Leu Gly Ser Tyr Tyr Val
            20                  25                  30

Ser Trp Tyr Gln Gln Lys Pro Gly Gln Ala Pro Val Leu Val Ile Tyr
        35                  40                  45

Asn Asp Asn Asn Arg Pro Ser Gly Ile Pro Glu Arg Phe Ser Gly Ser
50                  55                  60

Asn Ser Gly Asn Thr Ala Thr Leu Thr Ile Ser Gly Thr Gln Ala Glu
65                  70                  75                  80

Asp Glu Ala Asp Tyr Tyr Cys Ala Thr Tyr Asp Ser Ser Thr Asp Val
                85                  90                  95

Phe Gly Gly Gly Thr Lys Leu Thr Val Leu Gly
            100                 105

<210> SEQ ID NO 9
<211> LENGTH: 119
<212> TYPE: PRT
<213> ORGANISM: Human
<220> FEATURE:
<221> NAME/KEY: BINDING
<222> LOCATION: (26)..(34)
<223> OTHER INFORMATION: CDR1
<220> FEATURE:
<221> NAME/KEY: BINDING
<222> LOCATION: (49)..(65)
<223> OTHER INFORMATION: CDR2
<220> FEATURE:
<221> NAME/KEY: BINDING
<222> LOCATION: (98)..(108)
<223> OTHER INFORMATION: CDR3

<400> SEQUENCE: 9

Gln Val Gln Leu Val Gln Ser Gly Ala Glu Val Lys Lys Pro Gly Glu
1               5                   10                  15

Ser Leu Lys Ile Ser Cys Lys Gly Ser Tyr Ser Phe Ser Asn Tyr Trp
            20                  25                  30

Ile Gly Trp Val Arg Gln Met Pro Gly Lys Gly Leu Glu Trp Met Gly
        35                  40                  45

Phe Ile Asp Pro Asp Asp Ser Asp Thr Asn Tyr Ser Pro Ser Phe Gln
```

-continued

```
                  50                  55                  60
Gly Gln Val Thr Ile Ser Ala Asp Lys Ser Ile Ser Thr Ala Tyr Leu
 65                  70                  75                  80

Gln Trp Ser Ser Leu Lys Ala Ser Asp Thr Ala Met Tyr Tyr Cys Ala
                 85                  90                  95

Arg Ala Leu Tyr Met Gln Gly Gly Ser Phe Asp Ser Trp Gly Gln Gly
                100                 105                 110

Thr Leu Val Thr Val Ser Ser
        115

<210> SEQ ID NO 10
<211> LENGTH: 109
<212> TYPE: PRT
<213> ORGANISM: Human
<220> FEATURE:
<221> NAME/KEY: BINDING
<222> LOCATION: (23)..(33)
<223> OTHER INFORMATION: CDR1
<220> FEATURE:
<221> NAME/KEY: BINDING
<222> LOCATION: (49)..(55)
<223> OTHER INFORMATION: CDR2
<220> FEATURE:
<221> NAME/KEY: BINDING
<222> LOCATION: (88)..(97)
<223> OTHER INFORMATION: CDR3

<400> SEQUENCE: 10

Asp Ile Glu Leu Thr Gln Pro Pro Ser Val Ser Val Ala Pro Gly Gln
 1               5                  10                  15

Thr Ala Arg Ile Ser Cys Ser Gly Asp Asn Leu Gly Ser Tyr Tyr Val
                 20                  25                  30

Ser Trp Tyr Gln Gln Lys Pro Gly Gln Ala Pro Val Leu Val Ile Tyr
                 35                  40                  45

Arg Asp Thr Asp Arg Pro Ser Gly Ile Pro Glu Arg Phe Ser Gly Ser
 50                  55                  60

Asn Ser Gly Asn Thr Ala Thr Leu Thr Ile Ser Gly Thr Gln Ala Glu
 65                  70                  75                  80

Asp Glu Ala Asp Tyr Tyr Cys Gln Ser Tyr Asp Tyr Val Ser Asn
                 85                  90                  95

Gln Val Phe Gly Gly Gly Thr Lys Leu Thr Val Leu Gly
                100                 105

<210> SEQ ID NO 11
<211> LENGTH: 119
<212> TYPE: PRT
<213> ORGANISM: Human
<220> FEATURE:
<221> NAME/KEY: BINDING
<222> LOCATION: (26)..(34)
<223> OTHER INFORMATION: CDR1
<220> FEATURE:
<221> NAME/KEY: BINDING
<222> LOCATION: (49)..(65)
<223> OTHER INFORMATION: CDR2
<220> FEATURE:
<221> NAME/KEY: BINDING
<222> LOCATION: (98)..(108)
<223> OTHER INFORMATION: CDR3

<400> SEQUENCE: 11

Gln Val Gln Leu Val Gln Ser Gly Ala Glu Val Lys Lys Pro Gly Glu
 1               5                  10                  15

Ser Leu Lys Ile Ser Cys Lys Gly Ser Tyr Ser Phe Thr Asn Ser Trp
```

```
                    20                  25                  30
Ile Ser Trp Val Arg Gln Met Pro Gly Lys Gly Leu Glu Trp Met Gly
            35                  40                  45

Ile Ile Asp Pro Asp Asp Ser Tyr Thr Ser Tyr Ser Pro Ser Phe Gln
 50                  55                  60

Gly Gln Val Thr Ile Ser Ala Asp Lys Ser Ile Ser Thr Ala Tyr Leu
 65                  70                  75                  80

Gln Trp Ser Ser Leu Lys Ala Ser Asp Thr Ala Met Tyr Tyr Cys Ala
            85                  90                  95

Arg Gly Ala Gly Tyr Gly Arg Met Phe Gly Asp Val Trp Gly Gln Gly
            100                 105                 110

Thr Leu Val Thr Val Ser Ser
            115

<210> SEQ ID NO 12
<211> LENGTH: 108
<212> TYPE: PRT
<213> ORGANISM: Human
<220> FEATURE:
<221> NAME/KEY: BINDING
<222> LOCATION: (23)..(33)
<223> OTHER INFORMATION: CDR1
<220> FEATURE:
<221> NAME/KEY: BINDING
<222> LOCATION: (49)..(55)
<223> OTHER INFORMATION: CDR2
<220> FEATURE:
<221> NAME/KEY: BINDING
<222> LOCATION: (88)..(96)
<223> OTHER INFORMATION: CDR3

<400> SEQUENCE: 12

Asp Ile Glu Leu Thr Gln Pro Pro Ser Val Ser Val Ala Pro Gly Gln
 1               5                  10                  15

Thr Ala Arg Ile Ser Cys Ser Gly Asp Asn Leu Gly Ser Tyr Tyr Ala
            20                  25                  30

Ser Trp Tyr Gln Gln Lys Pro Gly Gln Ala Pro Val Leu Val Ile Tyr
            35                  40                  45

Gln Asp Asp Asn Arg Pro Ser Gly Ile Pro Glu Arg Phe Ser Gly Ser
 50                  55                  60

Asn Ser Gly Asn Thr Ala Thr Leu Thr Ile Ser Gly Thr Gln Ala Glu
 65                  70                  75                  80

Asp Glu Ala Asp Tyr Tyr Cys Gly Ala Tyr Thr Tyr Ser Thr Ser Trp
            85                  90                  95

Val Phe Gly Gly Gly Thr Lys Leu Thr Val Leu Gly
            100                 105

<210> SEQ ID NO 13
<211> LENGTH: 118
<212> TYPE: PRT
<213> ORGANISM: Human
<220> FEATURE:
<221> NAME/KEY: BINDING
<222> LOCATION: (26)..(37)
<223> OTHER INFORMATION: CDR1
<220> FEATURE:
<221> NAME/KEY: BINDING
<222> LOCATION: (52)..(67)
<223> OTHER INFORMATION: CDR2
<220> FEATURE:
<221> NAME/KEY: BINDING
<222> LOCATION: (100)..(107)
<223> OTHER INFORMATION: CDR3
```

```
<400> SEQUENCE: 13

Gln Val Gln Leu Lys Glu Ser Gly Pro Ala Leu Val Lys Pro Thr Gln
1               5                   10                  15

Thr Leu Thr Leu Thr Cys Thr Phe Ser Gly Leu Ser Leu Ser Thr Ser
            20                  25                  30

Gly Val Gly Val Gly Trp Ile Arg Gln Pro Pro Gly Lys Ala Leu Glu
        35                  40                  45

Trp Leu Ala Leu Ile Tyr Ser Asn Asp Asp Lys Arg Tyr Ser Thr Ser
    50                  55                  60

Leu Lys Thr Arg Leu Thr Ile Ser Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala Arg Tyr Lys Gln Glu Thr Ile Asp Tyr Trp Gly Gln Gly Thr
                100                 105                 110

Leu Val Thr Val Ser Ser
            115

<210> SEQ ID NO 14
<211> LENGTH: 105
<212> TYPE: PRT
<213> ORGANISM: Human
<220> FEATURE:
<221> NAME/KEY: BINDING
<222> LOCATION: (23)..(33)
<223> OTHER INFORMATION: CDR1
<220> FEATURE:
<221> NAME/KEY: BINDING
<222> LOCATION: (49)..(53)
<223> OTHER INFORMATION: CDR2
<220> FEATURE:
<221> NAME/KEY: BINDING
<222> LOCATION: (86)..(93)
<223> OTHER INFORMATION: CDR3

<400> SEQUENCE: 14

Asp Ile Glu Leu Thr Gln Pro Pro Ser Val Ser Val Ala Pro Gly Gln
1               5                   10                  15

Thr Ala Arg Ile Ser Cys Ser Gly Asp Asn Leu Gly Glu Lys Tyr Ala
            20                  25                  30

Tyr Trp Tyr Gln Gln Lys Pro Gly Gln Ala Pro Val Leu Val Ile Tyr
        35                  40                  45

Asp Asp Asn Asn Arg Gly Ile Pro Glu Arg Phe Ser Gly Ser Asn Ser
    50                  55                  60

Gly Asn Thr Ala Thr Leu Thr Ile Ser Gly Thr Gln Ala Glu Asp Glu
65                  70                  75                  80

Ala Asp Tyr Tyr Cys Gln Ser Tyr Asp Ile Glu Ile Thr Val Phe Gly
                85                  90                  95

Gly Gly Thr Lys Leu Thr Val Leu Gly
                100                 105
```